(12) United States Patent
Dormoy et al.

(10) Patent No.: US 6,417,400 B1
(45) Date of Patent: Jul. 9, 2002

(54) METHYL-PHENYL DERIVATIVES, PREPARATION METHOD AND USE

(75) Inventors: Jean-Robert Dormoy, Sisteron; Dominique Goubet, Les Matelles; Patrice Moreau, Saint-Gely-du-Fesc, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/646,629

(22) PCT Filed: Mar. 17, 1999

(86) PCT No.: PCT/FR99/00593

§ 371 (c)(1), (2), (4) Date: Oct. 23, 2000

(87) PCT Pub. No.: WO99/48861

PCT Pub. Date: Sep. 30, 1999

(30) Foreign Application Priority Data

Mar. 24, 1998  (FR) .............................. 98 03621

(51) Int. Cl.[7] .............................. C07C 249/00
(52) U.S. Cl. .................. 564/272; 564/265; 558/314
(58) Field of Search ................. 564/272, 265; 558/314

(56) References Cited

U.S. PATENT DOCUMENTS 5,288,895 A  2/1994  Bouisset et al.

FOREIGN PATENT DOCUMENTS

EP  0 566 468  10/1993

OTHER PUBLICATIONS

Chem Abstract 1994:244,636, Cullen et al 1994*

* cited by examiner

Primary Examiner—Samuel Barts
(74) Attorney, Agent, or Firm—Michael D. Alexander; Paul E. Dupont

(57) ABSTRACT

The present invention relates to:
  a) methylbiphenyl derivatives of general formula:

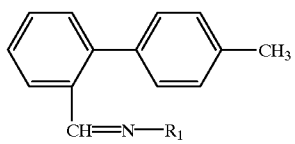

(I)

in which $R_1$ represents OH, $C_3$–$C_7$ alkyl or $C_3$–$C_7$ cycloalkyl, these compounds being in the form of individual isomers or mixtures thereof,
  b) their preparation by reaction:
    either of a hydroxylamine salt with an N-substituted o-(p-tolyl)benzaldimine, to give o-(p-tolyl) benzaldoxime
    or of an N-substituted 2-halobenzaldimine with a p-tolylmagnesium halide in the presence of an inorganic manganese derivative, to give the compounds of formula I in which $R_1$ represents $C_3$–$C_7$ alkyl or $C_3$–$C_7$ cycloalkyl
  c) their use for the preparation of o-(p-tolyl)-benzonitrile, which is an intermediate in the synthesis of medicinal products.

31 Claims, No Drawings

METHYL-PHENYL DERIVATIVES, PREPARATION METHOD AND USE

This application is a 371 of PCT/FR99/00593 filed Mar. 17, 1999.

The present invention relates in general to a novel methylbiphenyl derivative, to a process for its preparation and to its use as a synthetic intermediate.

More specifically, a subject of the invention is o-tolylbenzaldoxime of formula:

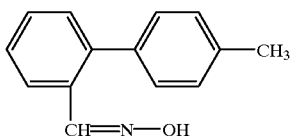

I.

this compound being considered in the form of its individual isomers or mixtures thereof.

The oxime derivative of formula I, referred to hereinbelow as OTBO, has been found to be particularly useful as an intermediate product, in particular for the preparation of o-(p-tolyl)benzonitrile, which is referred to hereinbelow as OTBN.

The latter compound may itself be widely used as a particularly advantageous intermediate, since it is the key intermediate in the synthesis of many active principles in medicinal products acting in particular against hypertension via an angiotensin II inhibitory mechanism.

OTBN was disclosed for the first time in patent EP 253 310 and a certain number of processes for synthesizing it have recently been proposed.

One of the processes which appears to be the most suitable for preparing OTBN was disclosed in patent EP 566 488. It consists of the reaction between an o-halobenzonitrile and a p-tolylmagnesium halide in the presence of a manganous salt, preferably $MnCl_2$. However, this method produces as a reaction by-product from 6.5% to 10% by weight of 4,4'-dimethylbiphenyl, referred to hereinbelow as bis-tolyl, resulting from the self-condensation of the p-tolylmagnesium halide.

In the context of the invention, the possibility of preparing OTBN via one of its potential precursors, in this instance o-(p-tolyl)benzaldoxime, was investigated with a view to solving the above problem.

To this end, attempts were made to apply a process similar to that of patent EP 253 310 also using p-tolylmagnesium bromide.

However, tests performed starting with 2-chlorobenzaldoxime and 3.5 equivalents of p-tolylmagnesium bromide, the reaction taking place in the presence of 0.36 equivalent of $MnCl_2$ in tetrahydrofuran at 90° C. and for 8 hours, did not produce the expected coupling reaction but rather the massive production of bis-tolyl.

The search for a process for preparing OTBN starting, for example, with the corresponding oxime, which is itself obtained in an advantageous manner and is free of the drawbacks mentioned above, remains of unquestionable interest.

It has now been found, surprisingly, that o-(p-tolyl) benzaldoxime can be obtained in excellent yields and with less than 6% bis-tolyl by-product by a coupling reaction using p-tolylmagnesium bromide and, rather than 2-chlorobenzaldoxime, an N-substituted 2-halobenzaldimine, so as to form an N-substituted o-(p-tolyl)benzaldimine which can readily be converted into the desired oxime.

According to the invention, this oxime of formula I is obtained by reacting a hydroxylamine salt with a benzaldimine derivative of general formula:

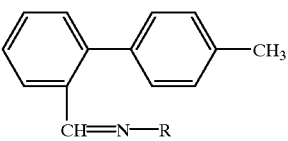

II.

in which R represents a linear or branched $C_3$–$C_7$ alkyl group or a $C_3$–$C_7$ cycloalkyl group, this compound of formula II being considered in the form of individual isomers or a mixture thereof, which gives the desired compounds.

This reaction usually takes place at a temperature of between 0° C. and 10° C., preferably between 0° C. and 5° C., and in an aprotic solvent.

In the context of the present invention, the expression "aprotic solvent" means a solvent such as an ether, generally an aliphatic or alicyclic ether, for example tetrahydrofuran, methyl tert-butyl ether, dibutyl ether or dioxane, an aliphatic or aromatic hydrocarbon, such as benzene, toluene or a xylene, or a halogenated hydrocarbon, such as dichloromethane, dichloroethane, chloroform or tetrachloroethane.

However, an ether is preferably used as solvent, for example tetrahydrofuran.

Moreover, the hydroxylamine salt, such as the hydrochloride or, preferably, the sulphate, is used in a proportion of from 1.5 to 2.5 molar equivalents per molar equivalent of benzaldimine derivative of formula II.

According to this method, OTBO can be obtained in yields of about 90% to 93% by weight.

The methylbiphenyl derivatives of formula II are novel and, in this respect, constitute another subject of the invention, whether they are in the form of individual isomers or a mixture thereof.

Consequently, the invention also relates, as novel intermediate products, to the benzaldimine derivatives of formula II in which R represents a linear or branched $C_3$–$C_7$ alkyl group or a $C_3$–$C_7$ cycloalkyl group, these benzaldimine derivatives being in the form of individual isomers or mixtures thereof.

Among these compounds of formula II, those in which R represents a tert-butyl group or, better still, a cyclohexyl group constitute preferred compounds.

The compounds of formula II can be prepared by reacting, in the presence of an inorganic manganese derivative, a benzaldimine derivative of general formula:

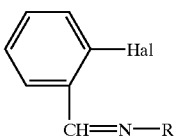

III.

in which R has the same meaning as above and Hal represents a halogen atom such as chlorine or bromine, this compound being in the form of individual isomers or mixtures thereof, with a p-tolylmagnesium halide, such as p-tolylmagnesium chloride or bromide, giving the desired compounds.

This coupling reaction is generally carried out in a suitable solvent and at a temperature of between –10° C. and the reflux temperature, preferably at the reflux temperature of the reaction medium.

The solvent usually envisaged is a compound of ether type such as an aliphatic or alicyclic ether, for example tetrahydrofuran, methyl tert-butyl ether, dibutyl ether or dioxane.

However, tetrahydrofuran is a preferred solvent.

In addition, the p-tolylmagnesium halide is generally used in excess, in particular in a proportion of from 1 to 2 molar equivalents per molar equivalent of compound of formula II, usually in a proportion of about 1.5 equivalents.

The inorganic manganese derivative is used in the reaction in a proportion of from 0.1 to 0.5 molar equivalent per molar equivalent of benzaldimine derivative of formula II, preferably from 0.15 to 0.30 molar equivalent.

This derivative is generally a manganese salt or oxide, but more particularly a manganous salt or manganous oxide. However, the manganous salt preferably corresponds to $MnCl_2$ or $MnCl_4Li_2$, it being possible for the latter to be formed in situ by adding two molar equivalents of LiCl and one molar equivalent of $MnCl_2$.

In this way, the compounds of formula II can be obtained in yields of at least 85% and with less than 6% bis-tolyl derivative.

For example, the preparation of o-(p-tolyl)-N-cyclohexylbenzaldimine starting with 0.4 mol of 2-chloro-N-cyclohexylbenzaldimine, 0.15 molar equivalent of $MnCl_2$ and 1.5 molar equivalents of p-tolylmagnesium chloride in tetrahydrofuran for 1 hour gave, along with an excellent yield of OTBN, only 5.5% bis-tolyl relative to the starting imine.

As regards the benzaldimine derivatives of formula III, these can be prepared by reaction, at a temperature between room temperature and the reflux temperature and in an aprotic solvent, preferably an ether, between a 2-chloro- or 2-bromobenzaldehyde and an amine of general formula:

R—NH$_2$  IV in which R has the same meaning as above, thus giving the desired compounds.

Since this reaction proceeds with the formation of water, it may be advantageous to carry it out in the presence of an agent for dehydrating the reaction medium, such as anhydrous magnesium sulphate.

As indicated above, the oxime derivative of formula I can be used to prepare OTBN.

Consequently, the invention relates to o-(p-tolyl) benzaldoxime as an intermediate for the final synthesis of OTBN.

Thus, OTBN can be obtained starting with the oxime derivative of formula I, for example by subjecting it to the action of a dehydrating agent.

The resulting reaction is usually carried out at a temperature of between room temperature and the reflux temperature of the medium, and in an aprotic solvent, preferably an ether such as tetrahydrofuran.

In the context of the invention, the expression "dehydrating agent" means an agent capable of converting the oxime function into a nitrile function, such as, for example, formic acid, phosphorus pentoxide, phosphorus oxychloride, pyridine or dicyclohexylcarbodiimide.

In addition, the dehydration reaction usually takes place in an aprotic solvent, preferably and advantageously in an ether such as, for example, tetrahydrofuran, and at a temperature of between room temperature and the reflux temperature, preferably at the reflux temperature of the reaction medium.

However, this dehydration reaction can be undertaken in the absence of solvent, the dehydrating agent itself acting as the solvent. Such is the case in particular for formic acid, which can be used both as dehydrating agent and as solvent in the context of the invention.

According to the above method, OTBN is obtained in yields of purified and crystallized product of greater than 85%, generally of about 90% to 95%, starting from OTBO.

The oxime of formula I and the benzaldimine derivatives of formula II involved in the final synthesis of OTBN can be used after isolation from the reaction medium in which they are formed.

Advantageously and preferably, however, OTBN is prepared in the same medium in which OTBO is formed, without the latter being isolated.

Consequently, the invention also relates to the preparation of OTBN starting with a benzaldimine derivative of formula II: either:

(a) by reacting this imine in an aprotic solvent with a hydroxylamine salt at a temperature of between 0° C. and 10° C., so as to form, transiently and without isolation, the oxime of formula I, which is treated with a dehydrating agent at a temperature of between room temperature and the reflux temperature, giving the desired compound; or:

(b) by reacting this imine with hydroxylamine-O-sulphonic acid ($H_2N$—O—$SO_3H$) in a two-phase medium formed from water and from an aprotic solvent and at a temperature of between room temperature and the reflux temperature, in order to obtain, transiently and without isolation, the oxime of formula I as a mixture with OTBN, this mixture being treated with a dehydrating agent at a temperature of between room temperature and the reflux temperature, giving the desired compound. This method, which usually takes place in an aprotic solvent, first gives a transient mixture of OTBN/OTBO, generally a mixture of 55% to 75% by weight of OTBN/45% to 25% by weight of OTBO, followed by OTBN itself in an overall yield of greater than 90% and less than 6% of bis-tolyl compound; or:

(c) by hydrolysing this imine, in an aprotic solvent, to give o-(p-tolyl)benzaldehyde, which is reacted with a hydroxylamine salt at a temperature of between 0° C. and 10° C., which gives, transiently and without isolation, the oxime of formula I, which is treated with a dehydrating agent at a temperature of between room temperature and the reflux temperature of the medium, giving the desired compound.

According to alternative embodiments, OTBO and thereafter OTBN can be prepared starting with the imine derivatives of formula III without isolating the intermediate products formed.

For example, an imine derivative of formula III under consideration is reacted, in an ether such as tetrahydrofuran, with a p-tolylmagnesium halide in the presence of an inorganic manganese derivative and, generally, at a temperature of between −10° C. and the reflux temperature, to form a benzaldimine derivative of formula II, which is then converted, without isolation from its reaction medium, into OTBO of formula I and then into OTBN according to one of the methods (a), (b) and (c) above.

The non-limiting examples which follow illustrate the invention.

In these examples, the following abbreviations have been used:

GC: gas chromatography
MS: mass spectrum
IR: infrared spectrum
NMR: nuclear magnetic resonance
OTBCI: o-tolyl-N-cyclohexylbenzaldimine
OTBO: o-(p-tolyl)benzaldoxime
OTBA: o-(p-tolyl)benzaldehyde
OTBTBI: o-(p-tolyl)-tert-butylbenzaldimine
t: retention time.

PREPARATIONS

A) 2-Chloro-N-cyclohexylbenzaldimine 9.70 g (0.0806 mol; 1.132 equivalents) of anhydrous magnesium sulphate are placed in a 50 ml two-necked round-bottomed flask equipped with a magnetic stirrer and on which is mounted an ascending condenser. A stream of nitrogen is passed through the round-bottomed flask for 10 minutes, and 8 ml (10.01 g; 0.0712 mol; 1 equivalent) of 2-chlorobenzaldehyde diluted in 20 ml of tetrahydrofuran are then added.

The mixture is maintained at reflux for 10 minutes with stirring (bath temperature=90° C.). 8.15 ml (7.07 g; 0.0713 mol; 1 equivalent) of cyclohexylamine are then added dropwise over 5 minutes so as not to break the reflux, which is continued for a further 2 hours.

In this way, a 2-chloro-N-cyclohexylbenzaldimine solution is obtained GC/MS: t (2-chloro-N-cyclohexylbenzaldimine)=9.92 min; m/z (ion, %)=223 ($M^+$/Cl 37,10); 222 ($M^+$–H/Cl 37,10); 221 ($M^+$/Cl 35,30); 221 ($M^+$–H/Cl 35,30)

IR ($CCl_4$): ν ($cm^{-1}$): 30,71 (weak, aromatic CH stretching); 2931 and 2856 (strong, alkyl CH stretching); 1636 (strong, CN stretching); 1592, 1568, 1470, 1450 and 1440 (medium to strong, aromatic CC stretching); 1383, 1346 and 1274 (medium to strong, deformation in the aromatic CH plane).

B) 2-Chloro-N-cyclohexylbenzaldimine 11 ml (13.728 g; 0.0977 mol) of 2-chlorobenzaldehyde are diluted in 50 ml of toluene followed by the addition, in a single portion, of 12 ml (10.404 g; 0.105 mol; 1.07 equivalents) of cyclohexylamine, which causes an exothermic reaction. The temperature rises from 18° C. to 38° C. The reaction mixture is then brought to reflux (bath temperature=124° C.). The solution becomes cloudy.

The water formed is removed using a Dean-Stark system and, after refluxing for 3 hours, the reaction is then stopped. The reaction mixture is cooled to room temperature and the toluene is evaporated off using a rotary evaporator, to give 20.22 g of a brownish viscous liquid (0.091 mol, i.e. a yield of 93.3%) which crystallizes slowly.

In this way, 2-chloro-N-cyclohexylbenzaldimine is obtained.

C) 2-Chloro-N-tert-butylbenzaldimine 11 ml (13.728 g; 0.0977 mol) of 2-chlorobenzaldehyde are added, with stirring, to 16 ml (11.136 g; 0.152 mol; 1.56 equivalents) of tert-butylamine in a 50 ml two-necked round-bottomed flask equipped with a magnetic stirrer and an ascending condenser, which gives rise to an exothermic reaction. The temperature rises from 16° C. to 37° C. A red fog then appears in the yellowish solution. 15 ml of toluene are then added, which makes the solution turn cloudy.

The final mixture is then maintained at 50° C. for 2 hours, and then at 127° C. for 1 hour in Dean-Stark apparatus so as to remove the water, and, after refluxing for 30 minutes, the reaction is stopped.

The solution is cooled to room temperature and the toluene is evaporated off on a rotary evaporator.

In this way, 17.99 g (0.092 mol) of 2-chloro-N-tert-butylbenzaldimine are obtained in the form of a yellowish viscous liquid which crystallizes slowly.

Yield: 94%

GC/MS: t=5.85 min; m/z (ion, %)=197 ($M^+$/Cl 37,1); 196 ($M^+$–H/Cl 37,1); 195 ($M^+$/Cl 35,5); 194 ($M^+$–H/Cl 35,5)

IR ($CCl_4$): ν ($cm^{-1}$): 3080, 2940 (weak, aromatic CH stretching); 2970 (strong, alkyl CH stretching); 1636 (strong, CN stretching); 1593, 1568, 1471 and 1441 (medium to strong, aromatic CC stretching); 1372 to 1274 (medium to strong, deformation in the aromatic CH plane).

EXAMPLE 1 o-(p-Tolyl)-N-cyclohexylbenzaldimine

The solution of 1 equivalent of 2-chloro-N-cyclohexylbenzaldimine obtained in Preparation A is filtered under nitrogen into a 250 ml three-necked round-bottomed flask containing 1.34 g (0.0106 mol; 0.15 equivalent) of manganese chloride, and the magnesium sulphate is washed with 58.85 ml of anhydrous tetrahydrofuran and under nitrogen. The filtrate obtained is then added to the above filtrate.

The final suspension thus obtained comprising 0.75 mol of 2-chloro-N-cyclohexylbenzaldimine is then maintained at reflux for 10 minutes (bath temperature=92° C.) with magnetic stirring, and 1.52 equivalents of p-tolylmagnesium chloride are added dropwise thereto at reflux over 30 minutes.

The suspension becomes dark, fleetingly turns green, becomes blood red and then ends up dark brown. After adding the magnesium derivative, the mixture is refluxed for 1 hour and a sample is then taken and treated with a water/ice mixture and extracted with diethyl ether. The organic phase is then analysed by gas chromatography, which reveals the desired compound as well as the presence of bis-tolyl, and traces of p-cresol and possibly of OTBA.

In this way, an o-(p-tolyl)-N-cyclohexylbenzaldimine solution is obtained.

GC/MS: t (OTBCI): 13.47 min; m/z (ion, %)=277 ($M^+$, 20); 276 ($M^+$–H, 100); 194 ($M^+$-cyclohexyl, 70).

By following the same process as above, but starting with 2-chloro-N-tert-butylbenzaldimine, o-(p-tolyl)-N-tert-butylbenzaldimine (Example 2) was prepared.

GC/MS: t (OTBTBI): 10.87 min; m/z (ion, %)=251 ($M^+$, 5); 250 ($M^+$–H, 10); 236 ($M^+$–$CH_3$, 70); 194 ($M^+$-tert-butyl, 100); 179 ($M^+$-tert-butyl-$CH_3$, 100).

EXAMPLE 3 o-(p-Tolyl)benzaldoxime

The reaction mixture obtained in Example 1 is cooled to room temperature without stirring, so as to settle out the inorganic species which precipitate (brown powder), and it is then added slowly, with stirring, into 150 ml of an ice-cold (0° C. to 5° C.) solution of 23.37 g (0.1424 mol; 2 equivalents) of hydroxylamine sulphate.

The two-phase mixture is then stirred vigorously for one hour and is allowed to warm to room temperature.

3 ml (2.65 g; 0.0226 mol; 2 equivalents relative to the manganese chloride) of N,N-diethyl-ethanolamine are then added to the mixture with stirring.

After 10 minutes, the stirring is stopped and the phases are allowed to separate by settling.

The upper organic phase is recovered and the aqueous phase is extracted with 3 times 100 ml of dichloromethane (pH of the aqueous phase=4). The total organic phase is dried over magnesium sulphate, filtered and then evaporated under vacuum using a rotary evaporator, to give 11.00 g of white flakes (overall chemical yield: 73% starting from 2-chlorobenzaldehyde, the amount of bis-tolyl by mass in the mixture being 4%).

50 ml of petroleum ether (30–40° C. fraction) are added to the solid thus obtained and the mixture is stirred for 15 minutes. The white solid formed is filtered off and rinsed under cold conditions with 10 ml of petroleum ether.

In this way, 10.62 g of o-(p-tolyl)benzaldoxime are collected in the form of white flakes no longer containing traces of bis-tolyl.

Crude overall yield: 67.5% starting from 2-chlorobenzaldehyde.

The oxime thus obtained can be recrystallized (dichloromethane/petroleum ether) to give white leaflets. Purity: 100%.

GC/MS: t (OTBO): 10.97 min; m/z (ion, %)=211 ($M^+$, 25); 210 ($M^+$–H, 100); 194 ($M^+$–OH, 60).

IR ($CCl_4$): ν ($cm^{-1}$) : 3596 (strong, free OH stretching, dilute solution); 3312 (weak, bound OH stretching); 3061, 3026 and 2924 (weak, aromatic CH stretching); 1516, 1480, 1447 and 1397 (weak to medium, aromatic CC stretching); 1260, 1200 and 1112 (weak to medium, deformation in the aromatic CH plane); 952 (strong, NO stretching).

$^1$H NMR: ($CDCl_3$) δ(ppm): 2.45 (broad s, 3H, $CH_3$); 7.28 (broad m, 4H, H8, H9, H11 and H12); 7.43 (broad m, 3H, H4, H5 and CHN); 7.95 (broad m, 1H, H3); 8.22 (broad s, 1H, H2) and 9.27 (broad, 1H, OH).

$^{13}$C NMR: ($CDCl_3$) δ(ppm): 21.22 ($CH_3$); 126.20; 127.53; 129.15; 129.59; 129.69; 129.84 and 130.37 (aromatic CHs); 136.56; 137.42 and 142.36 (aromatic C) and 149.85 (CH=NOH).

EXAMPLE 4 o-(p-Tolyl)benzaldehyde

The solution of 1 equivalent of 2-chloro-N-cyclohexylbenzaldimine obtained in Preparation A is filtered under nitrogen into a 250 ml three-necked round-bottomed flask containing 1.34 g (0.0106 mol; 0.15 equivalent) of manganese chloride, and the procedure as described in Example 1 is continued, in particular by adding 1.52 equivalents of p-tolylmagnesium chloride.

The reaction is then stopped by introduction into a mixture of 200 ml of water/ice and this mixture is extracted with 3 times 100 ml of dichloromethane after filtration through paper of a very viscous brown deposit. The total organic phase is dried over magnesium sulphate, filtered and then evaporated under vacuum, to give 16.29 9 of a brownish viscous liquid. The liquid obtained is absorbed onto silica and the solid formed is placed at the top of a column of silica prepared with petroleum ether (30–40° C. fraction). The column is eluted with this solvent until all of the bis-tolyl has been collected. 0.79 g (4.34 mmol) of a solid in crystalline form is thus recovered. The column is then eluted with a 5/95 v/v dichloromethane/petroleum ether mixture.

In this way, 10.05 g (51.26 mmol) of o-(p-tolyl) benzaldehyde are collected in the form of a yellowish viscous liquid.

Yield: 72%

GC/MS: t (OTBA): 8.78 min; m/z (ion, %)=196 ($M^+$, 75); 195 ($M^+$–H, 50); 181 ($M^+$–$CH_3$, 100); 167 ($M^+$–CHO, 40).

IR ($CCl_4$): δ($cm^{-1}$): 3066, 3028, 2924, 2848 and 2751 (weak, aromatic CH stretching); 1598, 1517, 1476, 1445 and 1392 (weak to medium, aromatic CC stretching); 1256 and 1194 (weak to medium, deformation in the aromatic CH plane).

$^1$H NMR: ($CDCl_3$) δ(ppm): 2.44 (s, 3H, $CH_3$); 7.26–7.28 (m, 4H, H8, H9, H11 and H12); 7.42–7.52 (m, 2H, H4 and H5); 7.59–7.64 (m, 1H, H3); 8.00–b 8.05 (m, 1H, H2) and 10.00 (s, 1H, CHO).

$^{13}$C NMR: ($CDCl_3$) δ(ppm); 21.21 ($CH_3$); 127.56; 128.95; 129.19; 129.87; 130.06; 130.81 and 133.53 (aromatic CHs); 133.80; 134.84; 138.04 and 146.01 (aromatic C) and 192.51 (CHO).

EXAMPLE 5 o-(p-Tolyl)benzaldoxime

The 10.05 g of o-(p-tolyl)benzaldehyde obtained in Example 4 are dissolved in 50 ml of tetrahydrofuran at room temperature and an aqueous solution of 16.83 g (0.1025 mol; 2 equivalents) of hydroxylamine sulphate is then added. The two-phase mixture is stirred vigorously at room temperature for 1 hour. A gas chromatographic analysis indicates the disappearance of the OTBA.

The upper organic phase is recovered and the aqueous phase is extracted with 3 times 50 ml of dichloromethane (pH of the aqueous phase=1). The organic phases are combined, dried over magnesium sulphate, filtered through a sinter funnel and evaporated under vacuum.

In this way, 10.07 g (0.0477 mol) of o-(p-tolyl) benzaldoxime are obtained.

Yield: 93%.

EXAMPLE 6 o-(p-Tolyl)benzonitrile 5 ml of formic acid are added to 0.54 g (2.56 mmol) of o-(p-tolyl)benzaldoxime. The suspension obtained is brought to reflux over 1 hour and maintained at this temperature for a further 1 hour (bath temperature: 126° C.).

The mixture dissolves at an internal temperature of 54° C.

The solution is cooled to room temperature, poured into water and extracted with diethyl ether. The ether phase is washed with 0.5N sodium hydroxide solution until the washing waters are basic (pH of about 9) and then with water until the washing waters are neutral (pH of about 7). The organic phase is dried over magnesium sulphate, filtered and evaporated under vacuum to give 0.45 g (2.33 mmol) of an oil which hardens over time.

In this way, o-(p-tolyl)benzonitrile is obtained in a yield of 91%.

Purity: >95%.

EXAMPLES 7 TO 9 o-(p-Tolyl)benzonitrile 1 molar equivalent of o-(p-tolyl)-N-cyclohexylbenzaldimine is dissolved in a 1/1 mixture of tetrahydrofuran/water and X molar equivalents of aminohydroxysulphonic acid are added. This mixture is maintained at a temperature T for 1 hour, which gives a mixture of OTBO/OTBN. This mixture is diluted in tetrahydrofuran, 10 molar equivalents of phosphorus pentoxide are then added and the mixture is allowed to react for a further 1 hour at room temperature.

The layer of dehydrating agent turns pink and the OTBO is recovered as a mixture with bis-tolyl (<5% by mass). After washing the phosphorus pentoxide layer with tetrahydrofuran, the solvent is evaporated off.

Depending on the starting amounts of aminohydroxysulphonic acid and the reaction temperature used, o-(p-tolyl)benzonitrile is obtained in the following yields:

| Ex. | X | T (° C.) | Mixture of OTBO/OTBN (% by weight) | Yield of OTBN |
|---|---|---|---|---|
| 7 | 1.9 | 20 | 55/45 | about 92% |
| 8 | 2.2 | 65 | 55/45 | about 92% |
| 9 | 3.1 | 90 | 75/25 | about 92% |

EXAMPLES 10 TO 12 o-(p-Tolyl)benzonitrile 1 molar equivalent of o-(p-tolyl)benzaldoxime is dissolved in the chosen solvent and the dehydrating agent is added. The medium is maintained at a temperature T for H hours. The medium is optionally filtered and is then poured into water and extracted with diethyl ether.

The ether phase is washed with 0.5N sodium hydroxide solution and then with water until neutral.

The resulting solution is dried over magnesium sulphate, filtered and evaporated under vacuum.

Depending on the solvents, dehydrating agent, temperature and reaction time used, o-(p-tolyl)benzonitrile is obtained in the following yields:

| Ex. | Dehydrating agent | Solvent | T (° C.) | H (hour) | % of OTBN Crude | Purified (crystallized) |
|---|---|---|---|---|---|---|
| 10 | Phosphorus pent-oxide (10 molar equivalents) | | 20 | 1 | 100 | 92 |
| 11 | DCC* (molar equivalent) | Methylene chloride | 20 | 24 | 100 | 86 |
| 12 | DCC (1 molar equivalent) | THF** | 90 | 4 | 100 | 90 |

*dicyclohexylcarbodiimide
**tetrahydrofuran

What is claimed is:
1. A methylbiphenyl derivative of general formula:

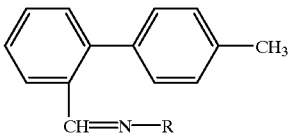

II in which R represents a linear or branched $C_3$–$C_7$ alkyl group or a $C_3$–$C_7$ cycloalkyl group, these compounds being considered in the form of their individual isomers or mixtures thereof.

2. A methylbiphenyl derivative of formula:

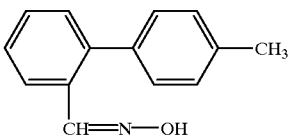

this compound being considered in the form of its individual isomers or mixtures thereof.

3. A methylbiphenyl derivative according to claim 1 wherein R represents cyclohexyl.

4. A methylbiphenyl derivative according to claim 1 wherein R represents tert-butyl.

5. A process for preparing a methyl-biphenyl derivative of formula:

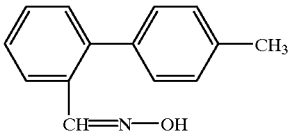

this compound being considered in the form of its individual isomers or mixtures thereof, wherein a hydroxylamine salt is reacted with a benzaldimine derivative according to claim 1 to give the desired compound.

6. A process according to claim 5 wherein the reaction takes place at a temperature of between 0° C. and 10° C.

7. A process according to claim 5 wherein the reaction is carried out in an aprotic solvent.

8. A process according to claim 7 wherein the aprotic solvent is an aliphatic or alicyclic ether, an aliphatic or aromatic hydrocarbon or a halogenated hydrocarbon.

9. A process according to claim 8 wherein the aprotic solvent is tetrahydrofuran, methyl tert-butyl ether, dibutyl ether or dioxane.

10. A process for preparing a methylbiphenyl derivative of general formula:

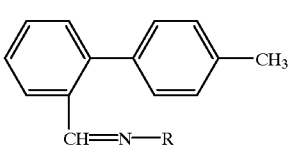

II in which R represents a linear or branched $C_3$–$C_7$ alkyl group or a $C_3$–$C_7$ cycloalkyl group, these compounds being considered in the form of their individual isomers or mixtures thereof wherein a benzaldimine derivative of general formula:

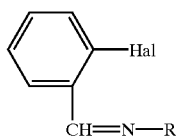

III in which R represents a linear or branched $C_3$–$C_7$ alkyl group or a $C_3$–$C_7$ cycloalkyl group and Hal represents a halogen atom, this compound being in the form of individual isomers or mixtures thereof, is reacted, in the presence of an inorganic manganese derivative, with a p-tolylmagnesium halide, to give the desired compounds.

11. A process according to claim 10 wherein the reaction takes place at a temperature of between −10° C. and the reflux temperature.

12. A process according to claim 10 wherein the reaction takes place in an aliphatic or alicyclic ether.

13. A process according to claim 12 wherein the ether is tetrahydrofuran, methyl tert-butyl ether, dibutyl ether or dioxane.

14. A process according to claim 10 wherein from 1 to 2 molar equivalents of p-tolylmagnesium chloride or bromide are used per molar equivalent of benzaldimine derivative of formula III.

15. A process according to claim 10 wherein the inorganic manganese derivative is a manganese salt or a manganese oxide.

16. A process according to claim 15 wherein the manganese salt is a manganous salt and the manganese oxide is manganous oxide.

17. A process according to claim 16 wherein, the manganous salt is $MnCl_2$ or $MnCl_4Li_2$.

18. A process according to claim 10 wherein the inorganic manganese derivative is used in a proportion of from 0.1 to 0.5 molar equivalent per molar equivalent of benzaldimine derivative of formula III.

19. A process for preparing o-(p-tolyl)benzonitrile wherein the methylbiphenyl derivative according to claim 2 is subjected to the action of a dehydrating agent.

20. A process according to claim 19 wherein the reaction produced is carried out at a temperature of between room temperature and the reflux temperature of the medium.

21. A process according to claim 19 wherein the reaction takes place in an aprotic solvent.

22. A process according to claim 21 wherein the aprotic solvent is an ether.

23. A process according to claim 19 wherein the dehydrating agent is formic acid, phosphorus pentoxide, phosphorus oxychloride, pyridine or dicyclohexylcarbodiimide.

24. A process for preparing o-(p-tolyl)benzonitrile wherein a benzaldimine derivative of formula II according to claim 1 is converted: either:
(a) by reacting this imine in an aprotic solvent with a hydroxylamine salt at a temperature of between 0° C. and 10° C., so as to form, transiently and without isolation, o-(p-tolyl)benzaldoxime, which is treated with a dehydrating agent at a temperature of between room temperature and the reflux temperature, giving the desired compound, or:
(b) by reacting this imine with hydroxylamine-O-sulphonic acid in a two-phase medium formed from water and from an aprotic solvent and at a temperature of between room temperature and the reflux temperature, in order to obtain, transiently and without isolation, o-(p-tolyl)-benzaldoxime as a mixture with o-(p-tolyl)-benzonitrile, this mixture being treated with a dehydrating agent at a temperature of between room temperature and the reflux temperature, giving the desired compound, or:
(c) by hydrolysing this imine, in an aprotic solvent, to give o-(p-tolyl)benzaldehyde, which is reacted with a hydroxylamine salt at a temperature of between 0° C. and 10° C., which gives, transiently and without isolation, o-(p-tolyl)benzaldoxime, which is treated with a dehydrating agent at a temperature of between room temperature and the reflux temperature of the medium, giving the desired compound.

25. A process according to claim 24 wherein the benzaldimine derivative of formula II is obtained by reaction between a benzaldimine derivative of general formula:

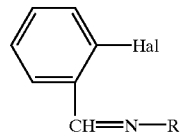

III in which R represents a linear or branched $C_3$–$C_7$ alkyl group or a $C_3$–$C_7$ cycloalkyl group, this compound being in the form of individual isomers or mixtures thereof, with a p-tolylmagnesium halide in the presence of an inorganic manganese derivative, and is then converted without isolation from its reaction medium.

26. A process according to claim 5 wherein R is cyclohexyl.

27. A process according to claim 5 wherein R is tert-butyl.

28. A process according to claim 10 wherein R is cyclohexyl.

29. A process according to claim 10 wherein R is tert-butyl.

30. A process according to claim 20 wherein the reaction takes places in an aprotic solvent.

31. A process according to claim 30 wherein the aprotic solvent is an ether.

* * * * *